(12) United States Patent
Wiedenhoefer et al.

(10) Patent No.: US 10,709,377 B2
(45) Date of Patent: Jul. 14, 2020

(54) SYSTEM AND METHODS FOR MONITORING AN ORTHOPEDIC IMPLANT AND REHABILITATION

(71) Applicant: Consensus Orthopedics, Inc., El Dorado Hills, CA (US)

(72) Inventors: Curt Wiedenhoefer, Davis, CA (US); Justin Anthony Creel, Fair Oaks, CA (US); Brian James Katerberg, Folsom, CA (US); Joshua Dale Howard, Sacramento, CA (US)

(73) Assignee: CONSENSUS ORTHOPEDICS, INC., El Dorado Hills, CA (US)

( * ) Notice: Subject to any disclaimer, the term of this patent is extended or adjusted under 35 U.S.C. 154(b) by 255 days.

(21) Appl. No.: 15/077,809

(22) Filed: Mar. 22, 2016

(65) Prior Publication Data
US 2016/0302721 A1    Oct. 20, 2016

Related U.S. Application Data

(60) Provisional application No. 62/136,892, filed on Mar. 23, 2015, provisional application No. 62/136,925, filed on Mar. 23, 2015.

(51) Int. Cl.
*A61B 5/11* (2006.01)
*A61B 5/00* (2006.01)
(Continued)

(52) U.S. Cl.
CPC ........ *A61B 5/4528* (2013.01); *A61B 1/00016* (2013.01); *A61B 1/041* (2013.01);
(Continued)

(58) Field of Classification Search
CPC ............ A61B 5/45; A61B 5/4528; A61B 5/11
See application file for complete search history.

(56) References Cited

U.S. PATENT DOCUMENTS 3,724,651 A    4/1973  Link
4,353,135 A   10/1982  Forte et al.
(Continued)

FOREIGN PATENT DOCUMENTS

EP         1938749 A2 *  7/2008  ............. A61B 5/112
WO      2008/120215      10/2008
(Continued)

OTHER PUBLICATIONS

U.S. Appl. No. 15/422,299, filed Feb. 1, 2017.
(Continued)

*Primary Examiner* — Michael J D Abreu
(74) *Attorney, Agent, or Firm* — Lowe Graham Jones PLLC; Bruce E. Black (57) ABSTRACT

A system for monitoring a joint of a patient includes multiple sensors to be disposed near a joint and to measure or observe actions or physical quantities associated with the joint; and at least one communications module coupled to the sensors to receive data from the sensors and to transmit sensor information to an external device. In some embodiments, the sensors are implantable near the joint. In other embodiments, the sensors are disposed in a sensor module that is positioned adjacent the skin of the patient near the joint.

20 Claims, 7 Drawing Sheets

(51) Int. Cl.
| | |
|---|---|
| *G01C 21/12* | (2006.01) |
| *A61B 1/00* | (2006.01) |
| *A61B 1/04* | (2006.01) |
| *A61B 5/107* | (2006.01) |
| *G01C 22/00* | (2006.01) |
| *G01C 9/00* | (2006.01) |
| *A61B 5/07* | (2006.01) |
| *A61B 34/20* | (2016.01) |
| *A61B 5/01* | (2006.01) |
| *A61B 5/024* | (2006.01) |
| *A61B 90/30* | (2016.01) |

(52) U.S. Cl.
CPC .......... *A61B 5/0013* (2013.01); *A61B 5/0015* (2013.01); *A61B 5/0031* (2013.01); *A61B 5/0035* (2013.01); *A61B 5/0086* (2013.01); *A61B 5/076* (2013.01); *A61B 5/1071* (2013.01); *A61B 5/1121* (2013.01); *A61B 5/1126* (2013.01); *A61B 5/4585* (2013.01); *G01C 9/00* (2013.01); *G01C 21/12* (2013.01); *G01C 22/006* (2013.01); *A61B 5/01* (2013.01); *A61B 5/024* (2013.01); *A61B 5/112* (2013.01); *A61B 5/4851* (2013.01); *A61B 5/686* (2013.01); *A61B 5/6833* (2013.01); *A61B 5/6878* (2013.01); *A61B 5/742* (2013.01); *A61B 2034/2048* (2016.02); *A61B 2090/309* (2016.02); *A61B 2505/09* (2013.01); *A61B 2560/0214* (2013.01); *A61B 2562/0219* (2013.01); *A61B 2562/0223* (2013.01); *A61B 2562/0247* (2013.01)

(56) References Cited

U.S. PATENT DOCUMENTS

| | | | |
|---|---|---|---|
| 4,756,312 | A | 7/1988 | Epley |
| 5,833,603 | A | 11/1998 | Kovacs et al. |
| 6,588,931 | B2 | 7/2003 | Betzner et al. |
| 2003/0069714 | A1 | 4/2003 | Wigley et al. |
| 2003/0163287 | A1 | 8/2003 | Vock et al. |
| 2004/0122334 | A1 | 6/2004 | Yamashiro |
| 2004/0167390 | A1 | 8/2004 | Alexander et al. |
| 2005/0010299 | A1 | 1/2005 | Disilvestro |
| 2007/0250286 | A1 | 10/2007 | Duncan et al. |
| 2008/0027296 | A1 | 1/2008 | Hadvary et al. |
| 2008/0311765 | A1 | 12/2008 | Chatterjee et al. |
| 2009/0309683 | A1 | 12/2009 | Cochran |
| 2010/0174189 | A1 | 7/2010 | Abraham |
| 2010/0228089 | A1 | 9/2010 | Hoffman et al. |
| 2011/0046558 | A1 | 2/2011 | Gravesen et al. |
| 2011/0208444 | A1 | 8/2011 | Solinsky |
| 2011/0288379 | A1* | 11/2011 | Wu .......... A61B 5/02 600/301 |
| 2012/0143135 | A1* | 6/2012 | Cole .......... A61M 5/158 604/164.04 |
| 2013/0211259 | A1 | 8/2013 | Komistek et al. |
| 2013/0217998 | A1* | 8/2013 | Mahfouz .......... G16H 50/50 600/409 |
| 2014/0049911 | A1 | 2/2014 | Corbin et al. |
| 2014/0114453 | A1 | 4/2014 | Bentley |
| 2014/0142864 | A1 | 5/2014 | Spears et al. |
| 2014/0275815 | A1 | 9/2014 | Stein et al. |
| 2014/0316526 | A1 | 10/2014 | Grotz |
| 2014/0358193 | A1 | 12/2014 | Lyons et al. |
| 2015/0003699 | A1 | 1/2015 | Davis et al. |
| 2015/0019135 | A1* | 1/2015 | Kacyvenski .......... A61B 5/0488 702/19 |
| 2015/0045700 | A1* | 2/2015 | Cavanagh .......... A61B 5/4528 600/595 |
| 2015/0230183 | A1 | 8/2015 | Stogaitis et al. |
| 2015/0238094 | A1 | 8/2015 | Lai et al. |
| 2016/0066843 | A1 | 3/2016 | Mensinger et al. |
| 2016/0220176 | A1 | 8/2016 | Desnerck et al. |
| 2016/0302721 | A1 | 10/2016 | Wiedenhoefer et al. |

FOREIGN PATENT DOCUMENTS

| | | |
|---|---|---|
| WO | 2010/088696 | 8/2010 |
| WO | 2013/072234 | 5/2013 |
| WO | 2016/029138 | 2/2016 |

OTHER PUBLICATIONS

U.S. Appl. No. 15/422,312, filed Feb. 1, 2017.
U.S. Appl. No. 15/422,320, filed Feb. 1, 2017.
U.S. Appl. No. 15/077,793, filed Mar. 22, 2016.
Martinson et al., "Implementation of motion capture support in smartphones," Department of Computer Science and Engineering, Chalmers University of Technology, Jan. 1, 2010, Retrieved from the Internet at http://studentarbeten.chalmers.se/publication/129442-implementation-of-motion-capture-support-in-smartphones.
Partial Search Report for PCT/US2016/023637 dated May 30, 2016.
International Search Report and Written Opinion for PCT/US2016/023637 dated Aug. 9, 2016.
International Search Report and Written Opinion for PCT/US2016/023632 dated May 31, 2016.
International Search Report and Written Opinion for PCT/US2018/016424 dated Mar. 28, 2018.
International Search Report and Written Opinion for PCT/US2018/016417 dated Mar. 29, 2018.
International Search Report and Written Opinion for PCT/US2018/016422 dated Apr. 16, 2018.
Official Communication for U.S. Appl. No. 15/422,299 dated Apr. 4, 2018.
Official Communication for U.S. Appl. No. 15/422,299 dated May 2, 2019.
Official Communication for U.S. Appl. No. 15/077,793 dated Oct. 25, 2018.
Official Communication for U.S. Appl. No. 15/077,793 dated Jul. 15, 2019.
Official Communication for U.S. Appl. No. 15/077,793 dated Mar. 21, 2019.

* cited by examiner

SYSTEM AND METHODS FOR MONITORING AN ORTHOPEDIC IMPLANT AND REHABILITATION

CROSS-REFERENCE TO RELATED APPLICATION(S)

This application claims the benefit of U.S. Provisional Patent Application Ser. No. 62/136,892 filed Mar. 23, 2015, and U.S. Provisional Patent Application Ser. No. 62/136,925 filed Mar. 23, 2015, both of which are incorporated herein by reference in their entirety.

FIELD

The present invention is directed to the area of orthopedic implants and rehabilitation. The present invention is also directed to systems and methods for monitoring an orthopedic implant and rehabilitation after orthopedic replacement surgery.

BACKGROUND

Joint replacement surgery is a common orthopedic procedure for joints such as the shoulder, hip, knee, ankle, and wrist. In situations where the patient has worn-out or damaged a joint, it is possible to replace the joint with an implant that can merge with the skeletal structure and restore pain free movement and function. Prior to implanting prosthetic components in a joint of a patient, a surgeon generally resects at least a portion of the patient's native bone in order to create a platform, recess, or cavity for receiving at least a portion of the prosthetic components being implanted. During the process of implanting the prosthetic components muscles and tendons must be repositioned and reattached.

The patient must go through physical therapy in order to recover from this major surgery. The patient must exercise regularly as well as push for flexibility and balance in muscles that have been displaced. While the goal is to have the patient extend their range of motion, there can be an increased risk of falls or over-extension that can damage the implant and injure the patient. If the patient does not push their rehabilitation and achieve the needed range of motion, they will find themselves with a stiff joint which may require an additional surgical operation (MUA—Manipulation Under Anesthesia) to achieve an adequate range of motion to maintain their active lifestyle. Measuring or monitoring the progress of the physical therapy can be problematic but is very useful for maintaining the patient's dedication and participation.

BRIEF SUMMARY

One embodiment is a system for monitoring a joint of a patient that includes multiple sensors to be disposed near a joint and to measure or observe actions or physical quantities associated with the joint; and at least one communications module coupled to the sensors to receive data from the sensors and to transmit sensor information to an external device.

In at least some embodiments, the at least one communication unit includes a sensor processor to receive the sensor data and a wireless communications unit to wirelessly transmit the sensor information to or through the external device. In at least some embodiments, at least one of the sensors is configured and arranged to be implanted in the patient.

In at least some embodiments, the system further includes a sensor module having a housing, the sensors disposed in the housing, and the at least one communication unit disposed in the housing, where the sensor module is configured and arranged to be disposed adjacent skin of the patient to monitor the joint. In at least some embodiments, the sensor module further includes an adhesive pad coupleable to the housing to adhesively adhere the sensor module to the skin of the patient for at least one hour. In at least some embodiments, the system further includes a wearable article to receive the sensor module within the wearable article and to be worn by the patient so that the sensor module is disposed near the joint.

In at least some embodiments, the sensors include at least one sensor to provide sensor data that can be processed to determine a range of motion of the joint. In at least some embodiments, the at least one sensor includes a first accelerometer in combination with at least one of a second accelerometer, a gyroscope, or a magnetometer. In at least some embodiments, the sensors include at least two proximity sensors to provide sensor data that can be processed to determine a number of repetitions of joint movement. In at least some embodiments, the sensors include at least one temperature sensor or pulse sensor.

In at least some embodiments, the system further includes a patient device to receive the sensor information from the at least one communications module and to process the sensor information and display the processed information for viewing by the patient. In at least some embodiments, the system further includes a clinician device to receive the sensor information from the at least one communications module or from a patient device and to process the sensor information and display the processed information for viewing by a clinician.

Another embodiment is a sensor module that includes a housing to be disposed near a joint of a patient and adjacent to skin of the patient; multiple sensors disposed within the housing; a sensor processor disposed within the housing and coupled to the plurality of sensors to receive sensor data from the plurality of sensors; and a communications unit disposed within the housing and coupled to the sensor processor to transmit sensor information, based on the sensor data, to an external device. The sensors include at least one sensor to provide sensor data that can be processed to determine a range of motion of the joint;

In at least some embodiments, the sensor module further includes an adhesive pad coupleable to the housing to adhesively adhere the sensor module to the skin of the patient for at least one hour. In at least some embodiments, the adhesive pad includes at least one first locating feature and the housing includes at least one second locating feature having a shape complementary to a shape of the at least one first locating feature to facilitate alignment of the adhesive pad with the housing. In at least some embodiments, one of the at least one first locating feature or the at least one second locating feature includes a magnet and another one of the at least one locating feature or the at least one second locating feature includes a second magnet or a magnetically attractive material to facilitate coupling of the adhesive pad to the housing.

In at least some embodiments, the sensor module further includes a wearable article to receive the housing of the sensor module within the wearable article and to be worn by the patient so that the housing of the sensor module is disposed near the joint.

In at least some embodiments, the sensors include a first accelerometer in combination with at least one of a second accelerometer, a gyroscope, or a magnetometer. In at least some embodiments, the sensors include at least two proximity sensors configured and arranged to provide sensor data that can be processed to determine a number of repetitions of joint movement. In at least some embodiments, the sensors include at least one temperature sensor or pulse sensor.

A further embodiment is a system for monitoring rehabilitation. The system includes multiple sensors to be disposed near a rehabilitation site on a patient to measure or observe actions or physical quantities associated with the rehabilitation; and at least one communications module coupled to the sensors to receive data from the sensors and to transmit sensor information to an external device.

Yet another embodiment is a sensor module including a housing to be disposed near a rehabilitation site of a patient and adjacent to skin of the patient; multiple sensors disposed within the housing; a sensor processor disposed within the housing and coupled to the sensors to receive sensor data from the sensors; and a communications unit disposed within the housing and coupled to the sensor processor to transmit sensor information, based on the sensor data, to an external device. The sensors include at least one sensor configured and arranged to provide sensor data that can be processed to determine a range of motion at the rehabilitation site.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of orthopedic implants and rehabilitation. The present invention is also directed to systems and methods for monitoring an orthopedic implant and rehabilitation after orthopedic replacement surgery.

A system, as described herein, can be used to monitor the healing process of the patient as well as monitor or verify the extent of the patient's activity. The system includes one or more sensors that can communicate with a processor that can produce information, based on the sensor readings and data, that can facilitate the patient or another user, such as a clinician, doctor, or physical therapist, monitoring the patient's activity, the status of the orthopedic implant or surrounding tissues, or the effects of rehabilitation or other therapy. It will be understood, however, that the systems, devices, and methods described herein can be used in the context of other surgeries or even rehabilitation without surgical intervention. The sensors, described below, are placed near a rehabilitation site, such as a surgical site or the body portion to be rehabilitated.

The system may also provide alerts if patient tissue becomes inflamed or if the effectiveness of, or compliance to, rehabilitation therapy is insufficient. In at least some embodiments, at least one sensor is implanted and, in some embodiments, all of the sensors may be implanted. In at least some embodiments, at least one sensor is external to the patient and, in some embodiments, all of the sensors are external. For example, one or more sensors may be provided on a device that is applied to the skin of the patient or is carried in a brace or other article (for example, socks, shirt, shorts, pants, glove, or the like) that is worn by the patient.

In at least some embodiments, the one or more sensors communicate with a sensor processor on the device containing or near the sensors. In at least some embodiments, the sensor processor, or, alternatively or additionally, the sensors, communicate with a processor of a patient device, such as a mobile phone, tablet, computer or the like, or with a processor of a clinician device, such as a mobile phone, tablet, computer or the like.

Figure 1:
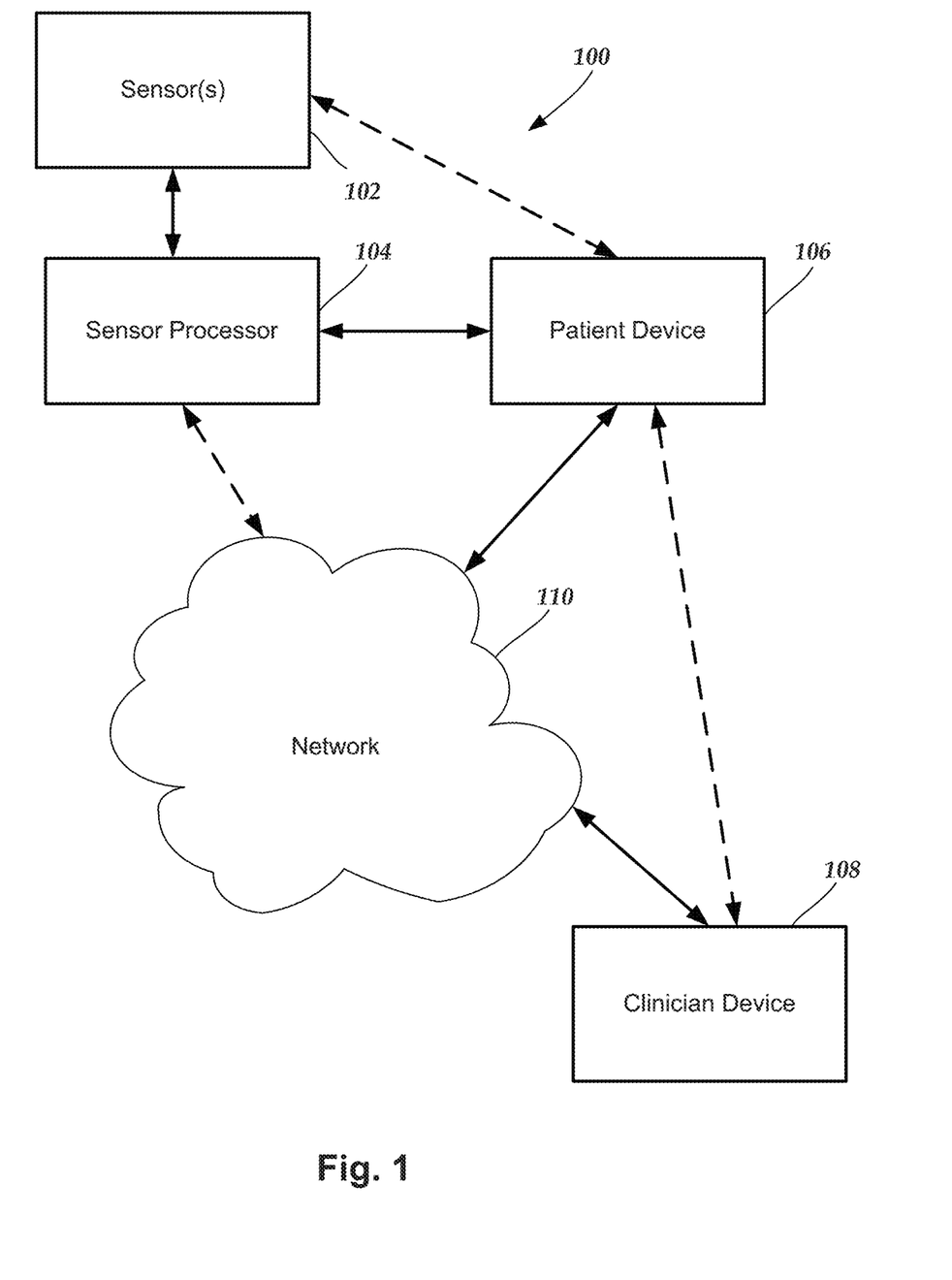
FIG. 1 is a schematic diagram of one embodiment of a system for monitoring rehabilitation of a patient after implant surgery, according to the invention.

FIG. 1 illustrates one embodiment of a system 100 for monitoring an orthopedic implant and rehabilitation after orthopedic replacement surgery. The system 100 includes one or more sensors 102, an optional sensor processor 104, a patient device 106, a clinician device 108, and a network 110. In other embodiments, the system may include fewer or more components, but the system typically includes the sensor(s) 102 and a processor (such as sensor processor 104, patient device 106, or clinician device 108) to communicate with the sensor(s) and provide information based on the sensor data. In at least some embodiments, the one or more sensors 102 may be combined into a sensor module that may also include the sensor processor 104.

In at least some embodiments, the one or more sensors 102 and the optional sensor processor 104 can be implanted into the patient. In other embodiments, the one or more sensors and the optional sensor processor 104 can be provided in a device that is external to the patient such as, for example, a device that is applied to the skin of the patient or is carried in a brace or other article or textile that is worn by the patient. In yet other embodiments, at least one of the sensors (or all of the sensors) are implanted and the optional sensor processor and, optionally, one or more sensors external to the patient.

In FIG. 1, the solid lines indicate communication between components in at least some embodiments of the system. Dotted lines indicate alternative or additional modes of communication between components. In addition to the communication illustrated in FIG. 1, in at least some embodiments, the sensor processor 104 or sensors 102 may also communicate directly with the clinician device. Communications can include, but is not limited to, wireless communication, wired communication, optical communication, ultrasonic communication, or the combination thereof. Satellite communication, cellular communication, Bluetooth™, near field communications (NFC), Infrared Data Association standard (IrDA), wireless fidelity (WiFi), and worldwide interoperability for microwave access (WiMAX) are non-limiting examples of wireless communication that can be used for communications. Ethernet, digital subscriber line (DSL), fiber to the home (FTTH), and plain old telephone service (POTS) are non-limiting examples of wired communication that can be used for communications.

The network 110 can be any suitable type of network including, but not limited to, a personal area network (PAN), local area network (LAN), metropolitan area network (MAN), wide area network (WAN), the Internet, or any combination thereof. In at least some embodiments, the network 110 can be bypassed to provide direct connection between components. It will be understood that other devices, such as a server or server farm, memory storage device, or the like can be connected to the patient device 106 or clinician device 108 through the network 110 or directly. For example, a server may be coupled to the patient device 106 or clinician device 108 that stores patient or other medical information, applications, user interfaces, a web interface, or the like for access by the patient device 106 or clinician device 108.

The patient device 106 and the clinician device 108 can be any of a variety of devices, such as computers (for example, a notebook computer, a mobile medical station or computer, a server, a mainframe computer, or a desktop computer), mobile devices (for example, a cellular phone or smartphone, personal digital assistant, or a tablet), or any other suitable device. In at least some embodiments, the clinician device 108 can be incorporated into a medical station or system.

Figure 2:
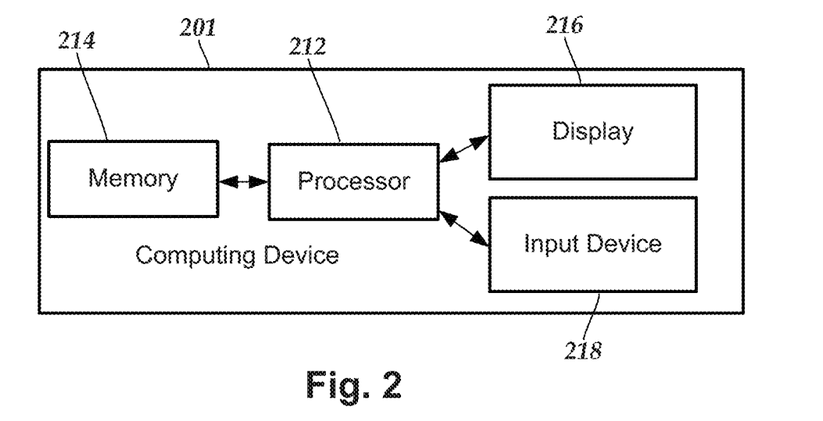
FIG. 2 is a schematic diagram of one embodiment of a computing device for use in the system of FIG. 1, according to the invention.

FIG. 2 illustrates one embodiment of a computing device 201 for use as the patient device 106 or clinician device 108. The computing device 201 includes a processor 212 and a memory 214, a display 216, and an input device 218. The computing device 201 can be local to the user or can include components that are non-local to the computer including one or both of the processor 212 or memory 214 (or portions thereof). For example, in some embodiments, the user may operate a terminal that is connected to a non-local processor or memory.

The computing device 201 can utilize any suitable processor 212 including one or more hardware processors that may be local to the user or non-local to the user or other components of the computing device. The processor 212 is configured to execute instructions provided to the processor. Such instructions can include any of the steps of methods or processes described herein.

Any suitable memory 214 can be used for the computing device 212. The memory 214 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 216 can be any suitable display device, such as a monitor, screen, display, or the like, and can include a printer. The input device 218 can be, for example, a keyboard, mouse, touch screen, track ball, joystick, voice recognition system, camera, microphone, or any combination thereof, or the like.

Returning to FIG. 1, the sensor processor 104 can be any suitable processor including one or more hardware processors. The sensor processor 104 is configured to execute instructions provided to the processor. The sensor processor 104 is configured to receive sensor data from the sensor(s) and communicate with the patient device 106, network 110, clinician device 108, or any combination thereof. Optionally, the sensor processor 104 may also process or analyze the sensor data and may have instructions stored thereon to perform such processing or analysis including, for example, instructions to perform the steps of any of the processing or analysis described herein. In at least some embodiments, one or more of the sensor(s) 102 can each include a processor that perhaps some or all of the functions of the sensor processor 104.

The one or more sensors 102 are provided to monitor the orthopedic implant and surrounding tissue or monitor rehabilitation after orthopedic surgery whether an implant was required or not, or to provide preparatory therapy in advance of a surgery, or any combination thereof. This disclosure will use an orthopedic knee implant as an example, but it will be understood that other joint implants, such as, for example, implants for the shoulder, hip, ankle, wrist, or any other joint, or any other orthopedic device, such as an orthopedic spinal implant, whether joint replacement, joint resurfacing, soft tissue reconstruction, debridement, limb correction surgery, ligament replacement, or the like.

Any suitable type of sensor 102 can be used including, but not limited to, accelerometers, magnetometers, gyroscopes, proximity sensors, infrared sensors, ultrasound sensors, thermistors or other temperature sensors, cameras, piezoelectric or other pressure sensors, sonar sensors, external fluid sensor, skin discoloration sensor, pH sensor, microphone, or the like or any combination thereof. In at least some embodiments, the system 100 includes at least one, two, three, four, five, six, or more different types of sensors 102. The system may include at least one, two, three, four, five, six, eight, ten, or more sensors 102.

The one or more sensors 102 can be used to measure, monitor, or otherwise observe one or more aspects of the orthopedic device, surrounding tissue, or patient activity, or the like. The following are examples of observations or measurements that can be made or interpreted using one or more of the sensors: number of steps, repetitions of an exercise, repetitions of joint movement (e.g., joint pivoting), type of exercise being performed, or other actions; stability, or lack thereof; flexion angle or range of motion; rate of motion; temperature of skin or internal tissues; pulse or pulse profile or heart rate recovery time after activity; particles in a joint space; ultrasound images, flow measurements, or Doppler measurements; sonar images, flow measurements, or Doppler measurements; pressure or load bearing measurements; detection of a limp or body orientation (e.g., subluxation, posture, scoliosis) or a change in body orientation; joint shock or impact monitoring; sleep profile or rest duration; gait analysis, body/limb/joint alignments; or the like. A system 100 can observe or measure one or more of these items or any combination of the items.

The following provides further details on some of these measurements or observations. One or more sensors (for example, accelerometers, gyroscopes, magnetometers, proximity sensors, or the like) may count steps or repetitions of an exercise or number of joint movements or other actions experienced by the sensor, and may be utilized to determine what type of exercise or movement is occurring. This can be used, for example, to monitor patient activity, monitor compliance with exercise therapy, or monitor possible signs of pain or other conditions that may hinder or aid rehabilitation. The sensor data may also be used to monitor changes in activity or trends in activity.

One or more sensors (for example, accelerometers, gyroscopes, magnetometers, proximity sensors, or the like) may sense or detect or compute the range of motion of the sensor, joint, or other portion of the patient body or the flexion of the joint. This can be used, for example, to monitor patient rehabilitation, patient activity, monitor compliance with exercise therapy, or monitor possible signs of pain or other conditions that may hinder or aid rehabilitation. These sensors or other sensors may be used to monitor shock to, or impact on, the orthopedic device or tissue around the orthopedic device. The sensor data may also be used to monitor changes in range of motion or flexion or trends in range of motion or flexion.

As an illustrative example, two proximity sensors (for example, a magnetometer and a magnet—such as a permanent magnet, electromagnet, or polymagnet or the like) can be implanted or placed externally on opposing sides of a joint. The distance between the two proximity sensors can be detected, measured, or otherwise observed. The distance between the two proximity sensors can be correlated to flexion or range of motion of the patient's joint. The variation in the distance between the two proximity sensors can be used to measure number of repetitions of joint motion or to monitor compliance with patient therapy. The variation in distance among repetitions or the trend in the variation among repetitions may be used to monitor improvement in joint flexibility or may indicate pain or other deleterious physical conditions of orthopedic implant or surrounding tissue. This information can be used to measure progress in the physical therapy following the surgery.

As another illustrative example, one or more accelerometers can measure the acceleration from joint movement. A ratio of measured acceleration between accelerometers of known distance apart can be used to assess the joint movement and region of motion or flexion by calculating the center of rotation about which the device is being rotated. This information can be used for the same purposes as described in the preceding example.

In another illustrative example, 1) an accelerometer and 2) a gyroscope or magnetometer (which indicates direction relative to magnetic north) can be used to measure range of motion, rate of motion, number of repetitions, or the like. This information can be used for the same purposes as described in the preceding two examples.

In another illustrative example, a single sensor such as an accelerometer, gyroscope, or magnetometer can be used to measure or otherwise observe range of motion, rate of motion, number of repetitions, or the like. In at least some embodiments, these measurements or other observations are determined using the sensor data and one or more assumptions about the sensor or sensor data based on, for example, the recognition of patterns in the sensor data, the upper and lower limits of the range in the data collected, or the like. Such information can be used in a manner similar to that in the preceding three examples.

One or more sensors (for example, thermistors or infrared sensors) may sense or detect or compute a temperature or a change in temperature or a temperature trend. The temperature may be a skin temperature or internal temperature of, for example, tissue near the orthopedic device. The temperature measurements may be used, for example, to indicate the possibility of inflammation or pain or another condition that may hinder rehabilitation or patient health. The temperature measurement may also be used, for example, to monitor if icing is being performed effectively, which can help reduce inflammation and aid healing. These sensors may also or alternatively be used to sense, detect, or measure a pulse, a change in pulse, trends in the patient's pulse, a pulse profile, or heart rate recovery after patient activity (such as exercise or other exertion). In addition, when a joint is immobilized by a cast, monitoring temperature and pulse can facilitate monitoring of the patient's health and possibility of inflammation or other deleterious condition.

One or more sensors (for example, ultrasound or sonar sensors or cameras or the like) can sense or detect or compute particles or density of particles or a particle density trend. These sensors may also be used to sense the tissue surrounding the orthopedic device, detect wear or dimensional changes on the orthopedic device or surrounding tissue, or the like. Ultrasound and sonar sensors may also be used to determine how close other parts of the knee (or other joint) are to the implant.

One or more sensors (for example, piezoelectric, strain gage, or other pressure or load bearing sensors) can sense or detect or compute pressure or load with or around the sensor or orthopedic device. The sensor data may also be used to monitor changes in range of pressure or load bearing or trends in pressure or load bearing. These sensors or other sensors may be used to monitor shock to, or impact on, the orthopedic device or tissue around the orthopedic device. A pressure or load bearing sensor may also be used to detect swelling of the tissue around the orthopedic implant. Multiple pressure or load bearing sensors may also be used to detect flexion (which may be indicated by a uniaxial stretching of the tissue) and swelling (which may be indicated by biaxial stretching of the tissue.)

Power can be provided to the sensors 102 and optional sensor processor 104 using any suitable power source including, but not limited to, primary cells, rechargeable batteries, storage capacitors, other power storage devices, or the like or any combination thereof. In some embodiments, the power can be provided by a kinetic energy power source that utilizes the movements of the patient's body to generate power for the components or to or to charge a battery or storage capacitor or other power storage device coupled to the components. In some embodiments, power can be provided by an induction power source disposed on or adjacent the patient's body (such as, for example, disposed in a brace or other article of clothing worn by the patient or in a mat upon which the patient sits or sleeps) and radiates electromagnetic energy to the sensors or optional sensor processor to power these components or to charge a battery or storage capacitor or other power storage device coupled to the components. Other wireless power sources can be used in place of the induction power source such as, for example, a wireless power source that utilizes ultrasound or WiFi or other rf power signals to generate power in the for charging a battery or storage capacitor or other power storage device.

In addition, for sensors or optional sensor processor disposed outside the body, a charging port can be provided for charging the battery or storage capacitor or other power storage device from a source such as a wall socket. It will be understood that in some embodiments there may be multiple methods for providing power to the component or to a power storage device associated with the component. All of the sensors and optional sensor processor may be coupled to the same power source or some of the sensors (or even all of the sensors) and sensor processor may have individual power sources.

In at least some embodiments, the sensors and optional sensor processor can be active at all times to measure, monitor, or otherwise observe. In other embodiments, one or more of the sensors and optional sensor processor can be active periodically (with a period of, for example, 15 or 30 seconds or 1, 5, 10, 15, or 30 minutes or 1, 2, 3, 4, 6, 12, or 24 hours) or randomly to measure, monitor, or otherwise observe. Optionally, the period may be programmable. In addition, the period may be optionally altered based on data from one or more of the sensors. In yet other embodiments, one or more of the sensors and optional sensor processor may be activated manually or automatically by the sensor module, patient device, clinician device, or other device. In at least some embodiments, the sensors and optional sensor processor may have different activation schedules (continuous, periodic, random, or manual). For example, a sensor to measure temperature may do so periodically, a sensor to measure number of steps or movement of the joint may be continuous, and a sensor to measure range of motion may be activated manually by the sensor module, patient device, or clinician device when the patient performs rehabilitation exercises.

Figure 3:
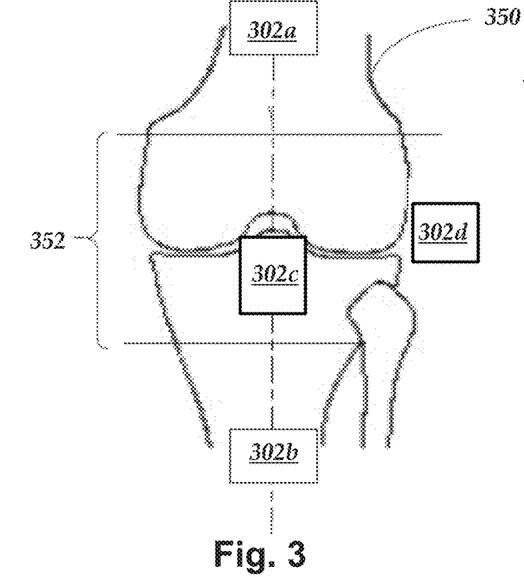
FIG. 3 is a schematic diagram of one embodiment of components of the system of FIG. 1 implanted near a knee replacement implant, according to the invention.

FIG. 3 illustrates a knee joint 350 having an orthopedic knee implant 352 and sensors 302a, 302b, 302c, 302d implanted around the knee joint 350. The orthopedic knee implant 352 can be made of, for example, surgical steel, carbon fiber, Kevlar fiber, or a combination thereof. To monitor the recovery of the joint 350, the set of sensors can, for example, include a first proximity sensor 302a, a second proximity sensor 302b, a thermal and acoustic sensor 302c, and a shock sensor 302d. It will be understood that other or different sensors can be used. The thermal and acoustic sensor 302c can be directly coupled to a portion of the orthopedic knee implant 352 or disposed in the tissue away from the device. The thermal and acoustic sensor 302c can detect any unexpected contact between the component parts of the orthopedic knee implant 352. Any acoustic noise or vibrations that come from the orthopedic knee implant 352 can be sampled and recorded by the thermal and acoustic sensor 302c. The thermal and acoustic sensor 302c may also be used to measure temperature of the implant 352 or surrounding tissue.

The shock sensor 302d can record or measure shocks or impacts to the implant 352. In at least some embodiments, the shock sensor 302d can be biased to only record shock or impact events over a preset threshold.

In at least some embodiments, the first proximity sensor 302a and the second proximity sensor 302b can be mounted along a centerline 212 of the joint to work in tandem. The distance between the first proximity sensor 302a and the second proximity sensor 302b can be detected and recorded. The distance between the first proximity sensor 302a and the second proximity sensor 302b can be correlated to the deflection of the orthopedic knee implant 352. This information can be used, for example, to measure progress in the physical therapy following the surgery to install the orthopedic knee implant 352. Other arrangements of sensors can be used to measure range of motion, as described herein. The proximity sensor 302a, 302b may also be used to observe or determine, for example, number of steps, number of joint movements, or exercise repetitions.

The sensors 302a, 302b, 302c, 302d communicate with the sensor processor 104), patient device 106, or clinician device 108 of FIG. 1. The sensor processor may be implanted with the body of the patient or may be disposed outside the body. For example, the patient can wear a knee brace that includes sensor processor and an optional induction power source used to power one or more of the sensors.

Figure 4:
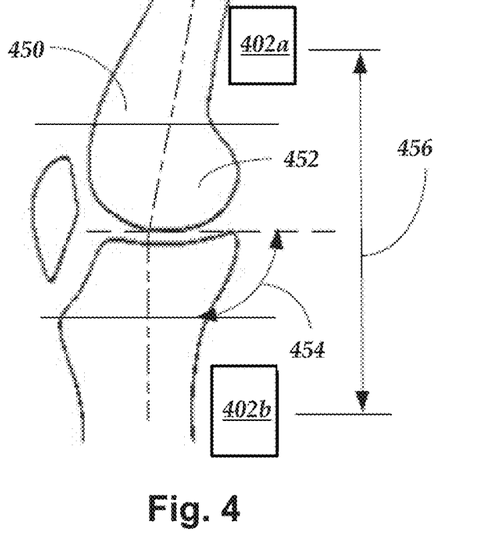
FIG. 4 is a schematic diagram of another embodiment of components of the system of FIG. 1 implanted near a knee replacement implant, according to the invention.

It will be recognized that other arrangements of sensors can be implanted during the surgery for placement of the orthopedic knee implant 352. FIG. 4 illustrates another knee joint 450 having an orthopedic knee implant 452 and sensors 402a, 402b implanted around the knee joint 450. The sensors 402a, 402b can be implanted in the tissue surrounding the knee joint, in the bone of the knee, or in the implant 452. If the orthopedic knee implant 452 is flexed in the direction of a deflection angle 454, by bending the knee, the separation distance 456 will be decreased until the flexing is reversed. The first proximity sensor 402a and the second proximity sensor 402b measure or otherwise observe the separation distance 456 which can then be used to determine the deflection angle 454. In at least some embodiments, the cycling of the deflection angle 454 can also be used as a step counter. It will be understood that other or different sensors can be used instead of, or in addition to, proximity sensors 402*a*, 402*b*.

Figure 5:
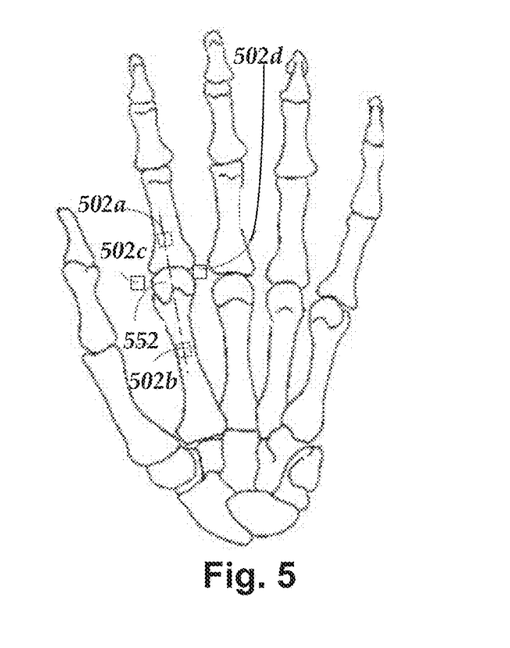
FIG. 5 is a schematic diagram of one embodiment of components of the system of FIG. 1 implanted near a finger joint replacement implant, according to the invention.

Similar techniques and arrangements can be used with other joints including, but not limited to, the finger joint, wrist joint, elbow joint, shoulder joint, hip joint, ankle joint, or toe joint. FIG. 5 illustrates one example of an arrangement disposed around a finger joint 550 with a finger joint implant 552, proximity sensors 502*a*, 502*b*, temperature sensor 502*c*, and pulse sensor 502*d*. The proximity sensors 502*a*, 502*b* can provide information similar to the embodiments described with respect to FIGS. 3 and 4. The temperature sensor 502*c* can be used to measure temperature of the implant 552 or surrounding tissue and the pulse sensor 502*d* can be used to measure the patient's pulse.

Figure 6:
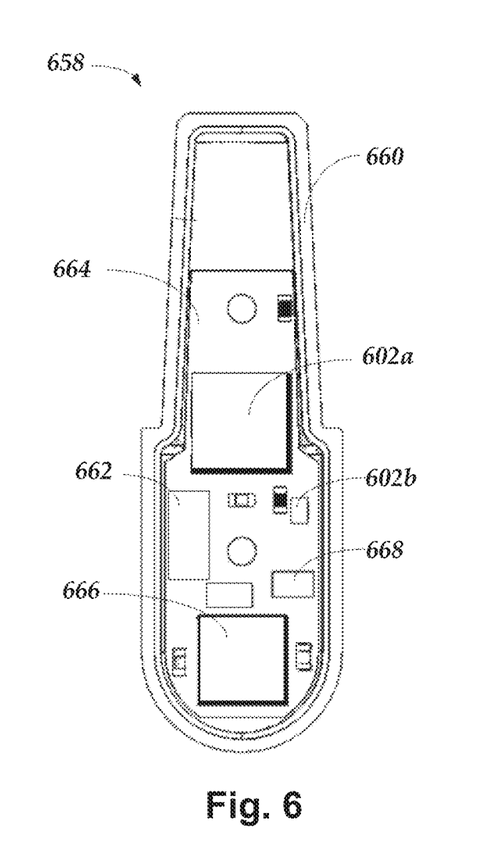
FIG. 6 is a schematic diagram of one embodiment of a sensor module that contains sensors for monitoring rehabilitation of a patient after implant surgery, according to the invention.

FIG. 6 illustrates one embodiment of an implantable sensor module 658 with one or more sensors 602*a*, 602*b*, a housing 660, a power source 662, a circuit carrier 664, a storage and communications unit 666, and a treatment unit 668. The one or more sensors can be any of the sensors described above including, for example, a proximity sensor and an acoustic sensor. Other embodiments of a sensor module can include more or fewer components.

The housing 660, can be formed of materials that are resistant to ingress of body fluids including metals, polymers, or the like such as, for example, polycarbonate, stainless steel, Kevlar fibers, or the like. The one or more sensors 602*a*, 602*b* can be mounted on a circuit carrier 664 (for example, a printed circuit board, a printed flex circuit, a semiconductor substrate, a glass substrate, or a printed Mylar substrate) and coupled to the power source 662. The storage and communication unit 612 can save the sensor data in a non-volatile storage device and pass the saved data through wireless or wired communication to the sensor processor 104, patient device 106, or clinician device 108 illustrated in FIG. 1. The optional treatment unit 668 may provide vibrations or pulses or release drugs that can enhance bone growth.

Figure 7A:
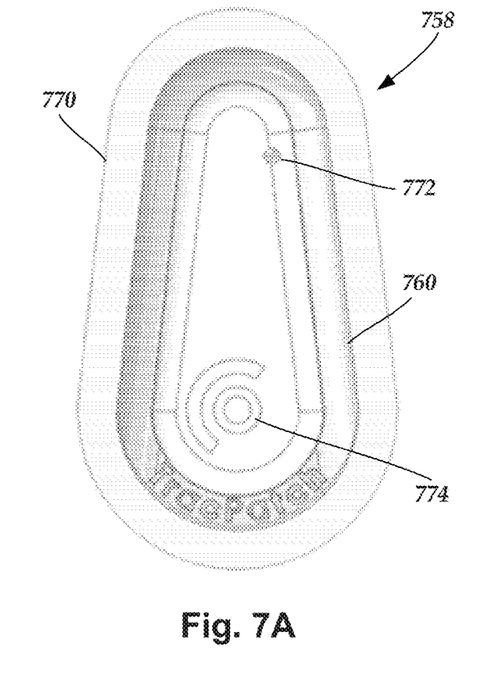
FIG. 7A is a top view of a second embodiment of a sensor module that contains sensors for monitoring rehabilitation of a patient after implant surgery, according to the invention.
Figure 7B:
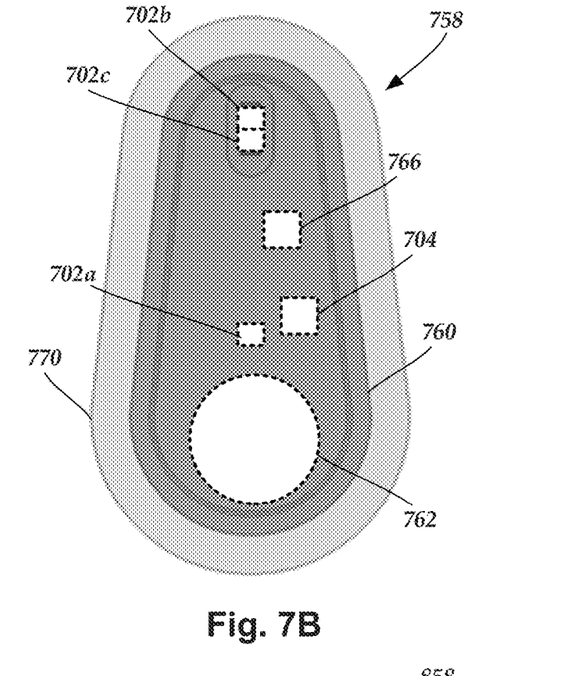
FIG. 7B is a bottom view of the sensor module of FIG. 7A, according to the invention.

FIGS. 7A and 7B are top and bottom views, respectively, of one embodiment of a sensor module 758 that can be adhered, or otherwise placed adjacent, to the skin of the patient. The sensor module includes a housing 760, optional adhesive pad 770, sensors 702*a*, 702*b*, 702*c*, power source 762, communications unit 766, and sensor processor 704. It will be recognized that other sensor modules may have more or fewer sensors and that the sensors may be the same or of different types.

The housing 760 can be made of any suitable material, such as plastic materials, and preferably has sufficient flexibility to fit comfortably on the patient's skin following the anatomical contours and to also flex as the patient moves. In at least some embodiments, the housing 760 is also water resistant to resist ingress of sweat, rain, and other fluids into the interior of the housing. In at least some embodiments, the housing 760 is sufficiently water resistant to allow the patient to shower with the sensor module 758 remaining attached to the skin of the patient and without any covering over the sensor module. In some embodiments, the housing 760 is sufficiently water resistant to allow the patient to bathe or swim without any covering over the sensor module 758.

In at least some embodiments, the housing 760 has a shape or indicia on the housing that visually indicates or suggests the orientation of the device when the housing is attached to the patient. In the illustrated embodiment, one end of the device is narrower than the other end which indicates or suggests to the user that the narrow end is pointed toward the knee or other joint.

The illustrated embodiment also features a power light 772 that is lit when the sensor module 758 is functioning to assure the patient that the device is operating. In some embodiments, the power light 772 may also flash or change color to indicate device functions such as, for example, a low battery, pairing with another device (for example, the patient device 106, clinician device 108, or network 110 of FIG. 1), actively taking readings using one or more of the sensors (particularly for sensors that are manually or periodically activated), alert the patient that it is time to perform exercises, change adhesives or the like.

The illustrated embodiment also features a power button 774 that can be activated to turn the device on and, optionally, to turn the device off. In at least some embodiments, the power button 774 may also be activated to manually direct one or more of the sensors to take readings.

The optional adhesive pad 770 is designed to hold the sensor module 758 on the patient's skin. The adhesive pad 770 can have, for example, a substrate with adhesive on both sides of the substrate so that one side can be adhered to the patient's skin and the other side adhered to the housing 760. In at least some embodiments, the adhesive pad 770 can be periodically replaced (for example, every 1, 2, 5, or 7 days or every 2, 3, 4, or more weeks) as the adhesive next to the patient's skin or the housing 760 may degrade or otherwise lose some or all of its adhesiveness. Preferably, at least the adhesive to be adhered to the patient's skin is selected to prevent or resist causing skin irritation. Preferably, the adhesive on both sides of the substrate is selected to be water resistant and resist losing adherence due to contact with sweat. In at least some embodiments, the adhesive pad 770 extends around the circumference of the sensor module 758, but includes one or more openings so allow the housing 760 to make contact with the skin of the patient or access to the patient without an intervening portion of the adhesive pad 770.

In other embodiments, instead of the adhesive pad 770, adhesive may be applied directly to the housing for adhering the housing with the directly to the skin. In yet other embodiments, instead of adhering the sensor module to the skin, the sensor module can be inserted into a brace or other item to be worn by the patient and hold the sensor module in place at the desired position on the body. This wearable item, such as a brace, optionally includes an opening that allows the sensor module to make contact with the skin of the patient.

The sensors 702*a*, 702*b*, 702*c*, power source 762, communications unit 766, and sensor processor 704 can be disposed within the housing 760. In some embodiments, a portion of one or more of the sensors, such as a temperature, pulse, or pressure sensor; moisture sensor, strain gage, may extend through the housing to provide contact with the skin or access to the patient without an intervening portion of the housing 760 or other parts of the sensor module 758. In some embodiments of the sensor module 758, sensor 702*a* is an accelerometer, sensor 702*b* is a gyroscope, and sensor 702*c* is a temperature sensor. The temperature sensor can be, for example, a thermistor or an infrared sensor. The accelerometer 702*a* and gyroscope 702*b* can be used to measure range of motion, number of steps, type of exercise, number of exercise repetitions or joint movements, and the like. In other embodiments, the sensors 702*a*, 702*b* can both be accelerometers that are optionally in-line with each other to increase accuracy in range of motion observations, and can be further utilized in the calculation of the point about which the motion is rotating. Yet other embodiments, the sensors include an accelerometer, a magnetometer, and a temperature sensor. As will be understood, any suitable sensor described above can be included in the sensor module and any combination of those sensors can be used in the sensor module. It is also understood that multiple sensor modules can be utilized together to provide data refinement or to provide comparative information, such as to show improvement in limp, or more accurately define the positions of both sides of the joint.

Any of the power sources described above can be used for a power source 762. For example, the power source 762 can be a primary cell and may have an expected lifetime under normal usage of at least 1, 2, or 4 weeks or at least 1, 2, 3, 4, 6, 8, 10, 12, 15, 18, 24, months or more. In some embodiments, the power source 762 is rechargeable using, for example, a recharge port in the sensor module 758 or is capable of being wirelessly charged such as with an inductive recharge device (such as an inductive mat or sleeve), or using WiFi or ultrasonic charging as described above. The power could be provided to the device by energy harvesting means, such as with cantilevered piezo reeds, a generator and pendulum setup, passive magnets rolling/sliding/bouncing through or by coils, or the like to convert some amount of kinetic energy into electrical energy to be used by the device. The power source 762 provides power to the sensors 702a, 702b, 702c, communications unit 766, sensor processor 704, and any other components in the sensor module.

The sensor processor 704 can be any suitable processor and may include, or be coupled to, a memory unit for storing sensor data. The sensor processor 704 can be wired or wirelessly coupled to the sensor 702a, 702b, 702c for receiving data from the sensors. In some embodiments, the sensor processor 704 may include analysis algorithms for analyzing or partially analyzing the sensor data. In other embodiments, the sensor processor 704 may be primarily designed to receive, store, and transmit sensor data.

The communications unit 766 can be any suitable communications arrangement that can transmit information from the sensor processor 704 or sensors 702a, 702b, 702c to another device (such as the patient device 106, clinician device 108, or network 110 of FIG. 1.) The communications unit 766 can transmit this information by any suitable wired or wireless technique including, but not limited to, Bluetooth™, near field communications, WiFi, infrared, radio frequency, acoustic, optical, or using a wired connection through a data port in the sensor module or any other communications technique presented herein or the like.

Figure 8A:
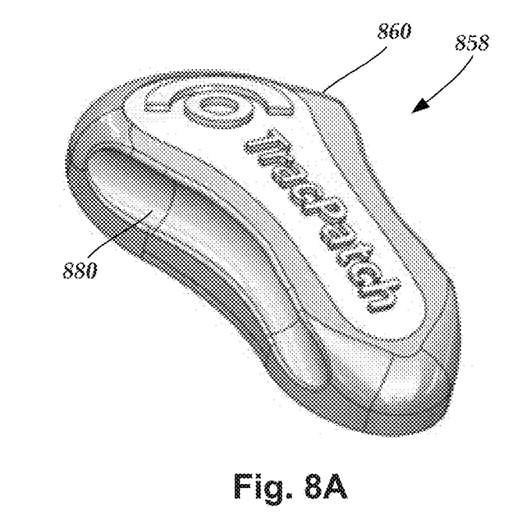
FIG. 8A is a top view of a third embodiment of a sensor module that contains sensors for monitoring rehabilitation of a patient after implant surgery, according to the invention.
Figure 8B:
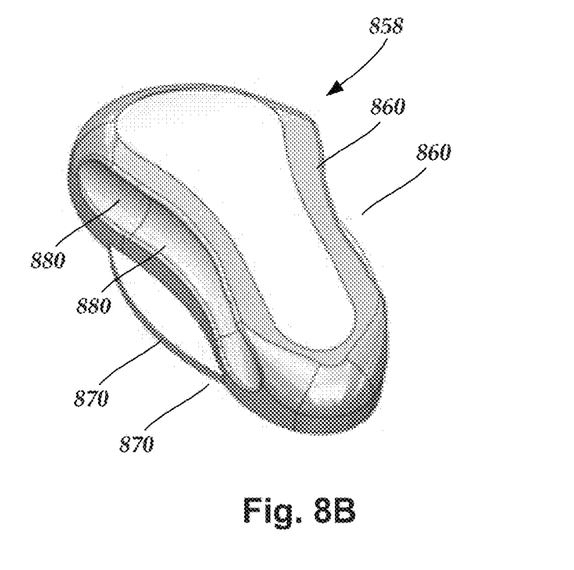
FIG. 8B is a top view of the sensor module of FIG. 8A with an adhesive pad, according to the invention.

FIGS. 8A and 8B illustrate another embodiment of a sensor module 858 without (FIG. 8A) and with (FIG. 8B) an adhesive pad 870. The sensor module 858 is similar to the sensor module 758 except in the shape of the adhesive pad 870 and that the housing 860 of this embodiment has pulling features 880 that facilitate gripping the sensor module 858 to more easily remove or pull the sensor module from the skin of the patient.

Figure 9A:
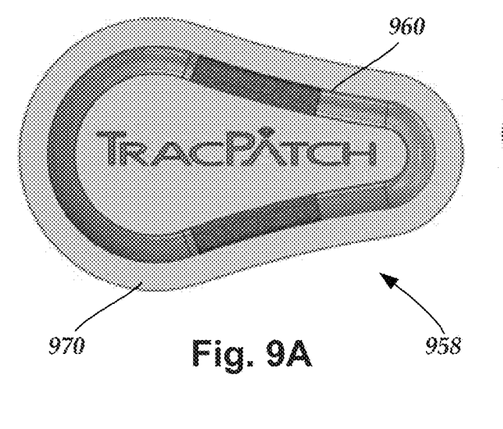
FIG. 9A is a top view of a fourth embodiment of a sensor module that contains sensors for monitoring rehabilitation of a patient after implant surgery, according to the invention.
Figure 9B:
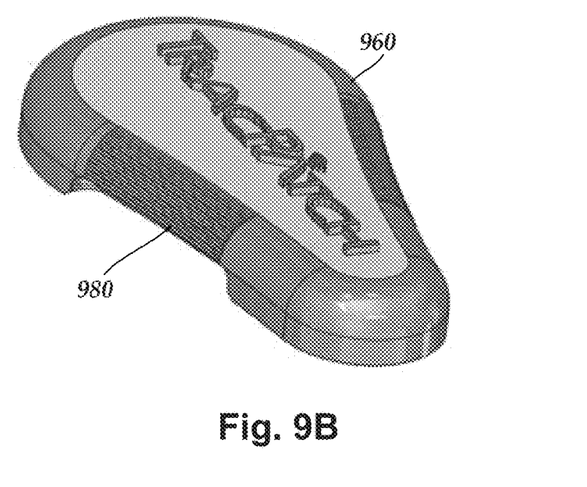
FIG. 9B is a top view of the sensor module of FIG. 8A without the adhesive pad, according to the invention.

FIG. 9A illustrates another embodiments of a sensor module 958 with a housing 960 and an adhesive pad 970. The sensor module 958 is similar to the sensor module 758 except as described below. FIG. 9B illustrates the housing 960 with gripping features that facilitate gripping the sensor module 958 to more easily remove or pull the sensor module from the skin of the patient.

Figure 9C:
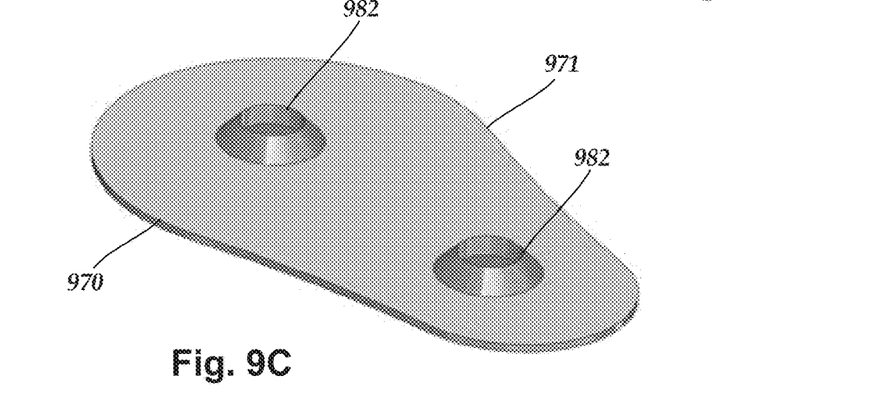
FIG. 9C is a top view of one embodiment of an adhesive pad for the sensor module of FIG. 8A, according to the invention.
Figure 9D:
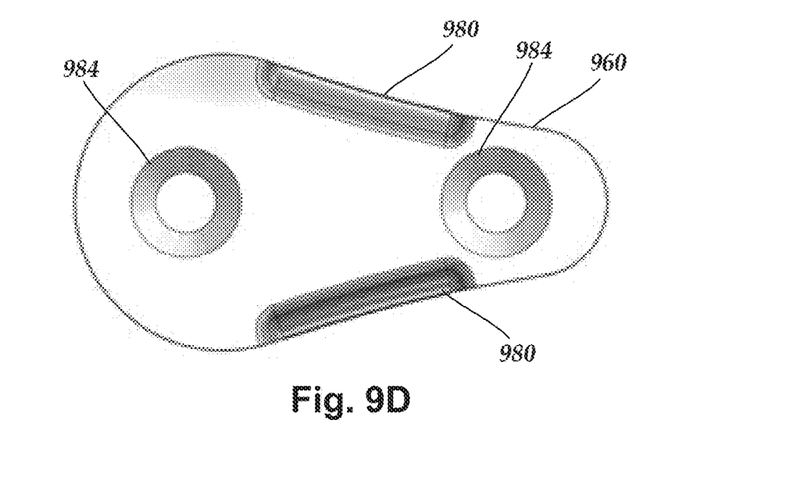
FIG. 9D is a bottom view of one embodiment of the sensor module of FIG. 9A for use with the adhesive pad of FIG. 9C, according to the invention.

FIG. 9C illustrates the adhesive pad 970 with one or more shaped locating features 982 attached to the adhesive pad and extending away from a substrate 971 of the adhesive pad. FIG. 9D illustrates the bottom of the housing 960 with one or more shaped locating features 984 that are preferably complementary in shape to the locating features 982 of the adhesive pad 970. The locating features 982, 984 facilitate properly attached the adhesive pad 970 to the housing 960.

In some embodiments, a second sensor module can be used. For example, the second sensor module can be placed on the same leg on the other side of the joint and the sensors in the two sensor module can be used to measure flexion angles, range of motion, and the like. The two sensor modules optionally can communicate with each other. As another example, a second sensor module may be placed on the other leg for use in detecting or observing limp or other gait deficiencies or placed on the torso to detect or observe body orientation. A second sensor module (or more additional sensor modules) may also be used when two or more replacements are implanted in the body, for example, with multiple joint or vertebra replacements, to detect or observe, for example, subluxations, changes or defects in posture, scoliosis, or the like.

In at least some embodiments, each of the locating features 982, 984 has a magnet to facilitate proper attachment and continued attachment of the housing 960 to the adhesive pad 970. Alternatively, one set of locating features 982, 984 may have a magnet and the other set have a magnetically attractive material. In at least some of these embodiments, the adhesive pad 970 optionally has adhesive on the side of the pad containing the locating features 982, 984.

U.S. patent application Ser. No. 15/077,793, filed on Mar. 22, 2016, incorporated herein by reference in its entirety, includes other systems and methods of using sensors, such as a camera, for monitoring a joint or other surgical site.

Figure 10:
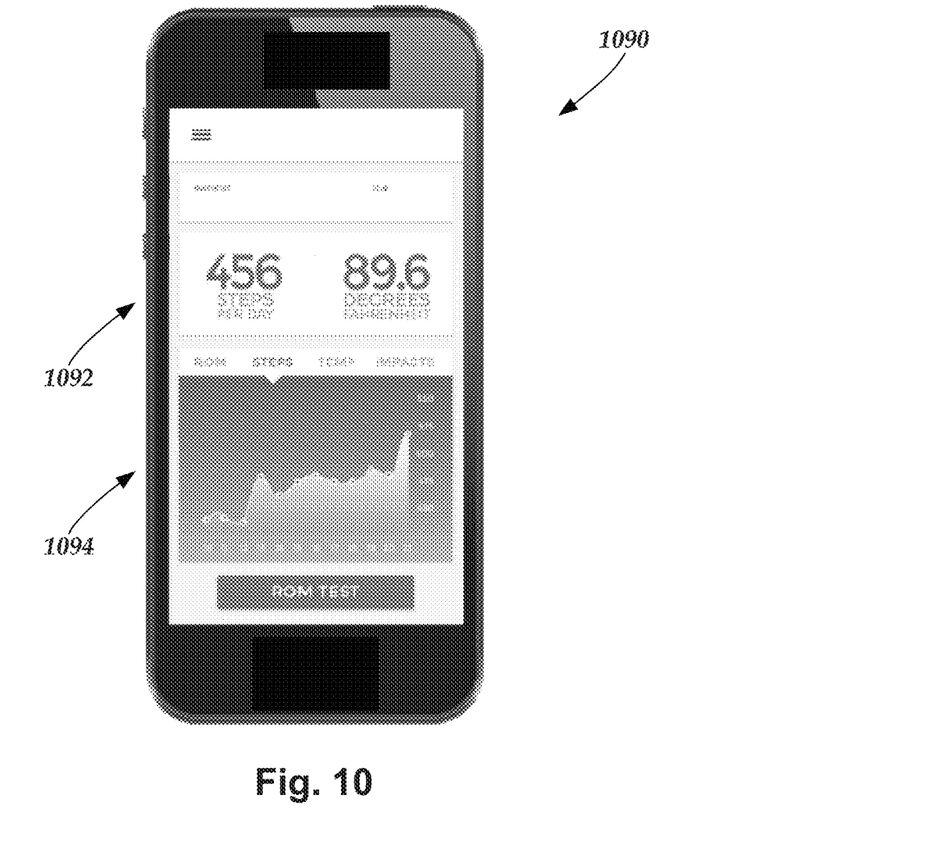
FIG. 10 is a diagram of one embodiment of a user interface for a mobile device to display information obtained from a sensor module, according to the invention.

As indicated above, the sensor processor or sensor communicate with a patient device or clinician device to provide sensor data or information derived from the sensor data. FIG. 10 illustrates one embodiment of a user interface 1090 for the patient device or clinician device. The illustrated user interface 1090 is particularly useful for a mobile device such as a smartphone or tablet. The user interface 1090 can provide information such as steps per day (or number of repetitions of an exercise or the like) and a temperature measurement as shown in section 1092. The user interface 1090 may also include a section 1092 that shows graphs of the data such as the hourly number of steps, as illustrated in FIG. 10. The illustrated user interface 1090 permits the user to select from other charts such as exercise history (labeled "ROM"), temperature, and number of impacts or shocks to the sensor module. It will be understood that other measurement or observations from the sensor described above can be graphed. In at least some embodiments, the user may also be able to select the time period of the graph to display data in periods of time such as, for example, minutes, hours, days, or weeks.

This user interface can be useful in monitoring patient activity and progress. The graphs in section 1094 may be useful for showing patient exercise history and progress. In some embodiments, the user interface may also allow the user to set goals such as, for example, a number of steps or a number of exercise repetitions over a particular period (for example, 1, 2, 4, 6, or 12 hours or 1 day or 1 week). The user interface may also display the current status towards attaining those goals. The user interface may also highlight notable events, such as, for example, the largest number of steps or exercise repetitions, elevated temperature readings, large numbers of impacts or shocks, or the like. The user interface may also highlight the attainment of goals.

Figure 11:
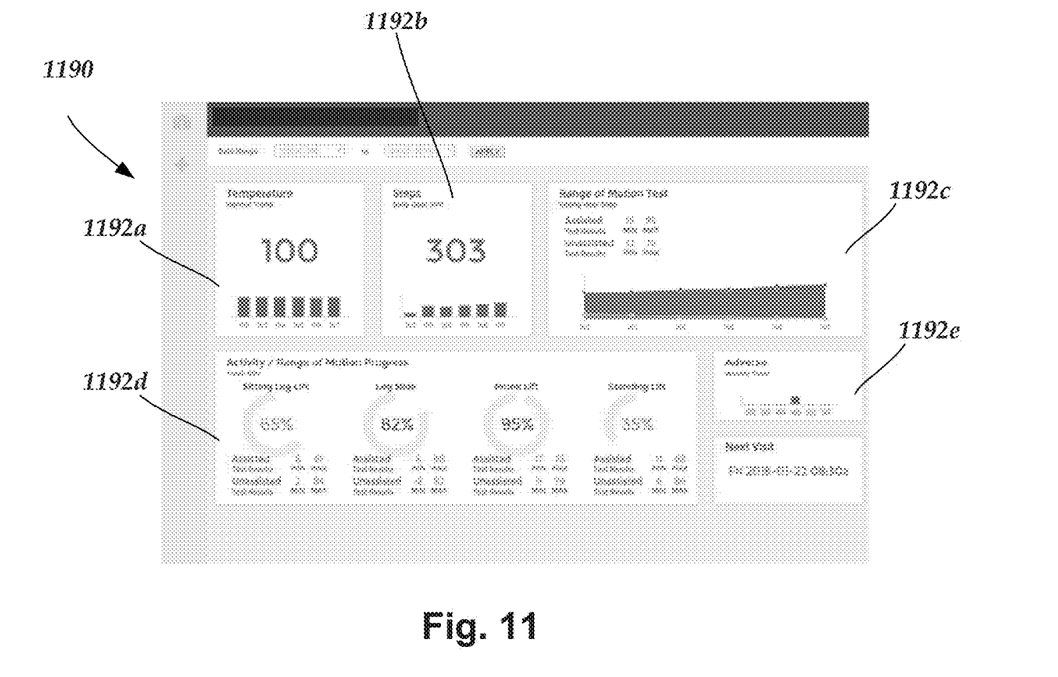
FIG. 11 is a diagram of another embodiment of a user interface to display information obtained from a sensor module, according to the invention.

FIG. 11 illustrates a user interface 1190 that may be suitable for a computer or web interface. The illustrated user interface includes a region 1192 displaying the results of temperature measurements 1192a, step measurements 1192b, range of motion tests 1192c, specific exercises and tests 1192d, and adverse events 1192e. These results may include numerical information and graphical information. These results may also illustrate graphically or numerically the degree of success in performing exercises (see, for example, region 1092d) and may also illustrate the degree of compliance with rehabilitation activities (such as the number of exercise repetitions performed). Such an arrangement of information can facilitate monitoring or patient progress, identification of progress or lack of progress, identification of concerns (such as elevated temperature or elevated number of shocks or impacts), and the like.

Figure 12:
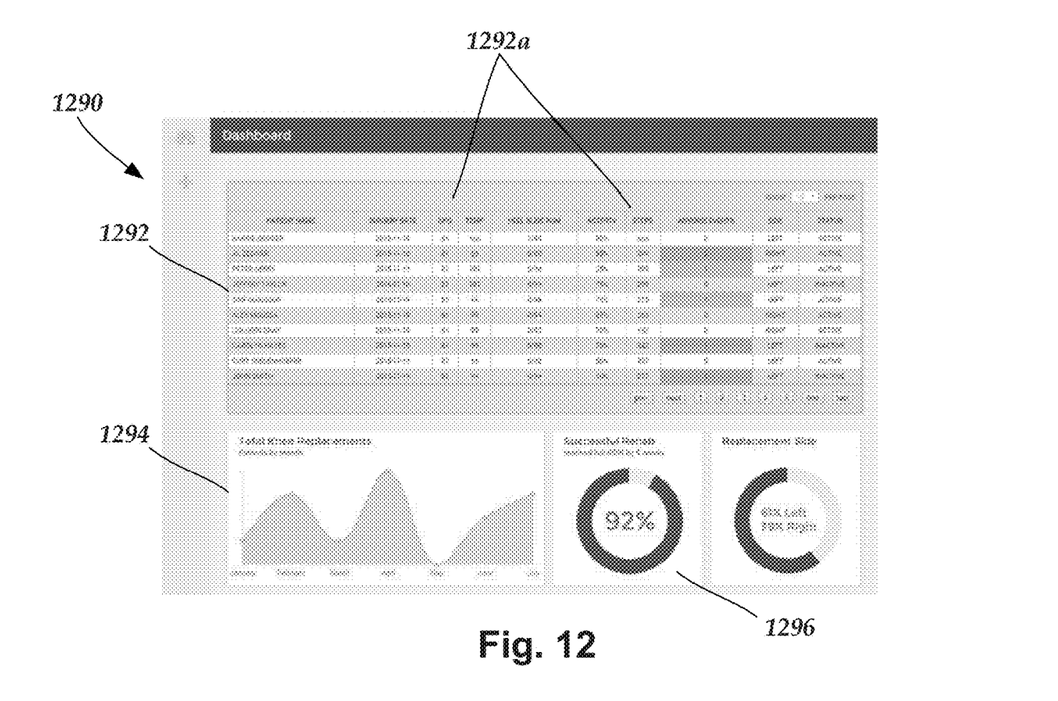
FIG. 12 is a diagram of a third embodiment of a user interface for a mobile device to display information obtained from a sensor module, according to the invention.

FIG. 12 illustrates a user interface 1290 for a clinician to monitor multiple patients. The region 1292 includes information such as patient name, surgery date, sensor date and results of tests 1292a, number of adverse events, location of the orthopedic implant, and the like. The clinician may also track number of surgeries 1294, rate of successful rehabilitation 1296, and other suitable information.

In at least some embodiments, the user interfaces 1090, 1190, 1290 can be web or application interfaces that are accessible when the patient device or clinician device accesses a server for a content provider. In at least some embodiments, the server or other servers or memory storage devices can store information for the web interface and may also store patient-specific information including patient identification data, sensor data or information derived from sensor data, patient or clinician comments or the like, or any other suitable data. In at least some embodiments, the patient-specific information can be accessed from the patient device, clinician device or other device which, in some embodiments, may require providing credentials (e.g., username or password or both) to access the information.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A system for monitoring a joint of a patient, the system comprising:
    a mechanically independent sensor module configured to be positioned on skin of the patient near the joint, the sensor module comprising
        a single housing, wherein the housing has a first end and a second end opposite the first end, wherein the second end is narrower than the first end indicating to the patient that the second end is to be positioned on the skin of the patient pointed toward the joint;
        a plurality of sensors disposed within the single housing configured and arranged to measure or observe actions or physical quantities associated with the joint, wherein the plurality of sensors comprises a) a temperature sensor and b) at least one of a first accelerometer, a gyroscope, or a magnetometer; and
        at least one communications module disposed within the single housing and coupled to the plurality of sensors and configured and arranged to receive data from the sensors and configured and arranged to transmit sensor information to an external device; and
        either a) adhesive directly disposed on the single housing or b) an adhesive pad coupled, or coupleable, to the single housing, wherein the adhesive or adhesive pad is configured adhere the sensor module to the skin of the patient.

2. The system of claim 1, further comprising a second sensor module that is mechanically independent from the sensor module, wherein the second sensor module comprises
    a single second housing;
    a plurality of second sensors disposed within the single second housing and configured and arranged to measure or observe actions or physical quantities associated with the joint; and
    at least one second communications module disposed within the single second housing and coupled to the plurality of second sensors and configured and arranged to receive data from the second sensors and configured and arranged to transmit sensor information to the external device.

3. The system of claim 2, wherein the plurality of sensors comprises a first proximity sensor and the second plurality of sensors comprises a second proximity sensor, wherein the first and second proximity sensors, in combination, are configured and arranged to provide sensor data that can be processed to determine a number of repetitions of joint movement.

4. The system of claim 1, wherein the system comprises the adhesive pad and the adhesive pad comprises at least one first locating feature and the housing comprises at least one second locating feature to facilitate alignment of the adhesive pad with the housing.

5. The system of claim 4, wherein the at least one second locating feature has a shape complementary to a shape of the at least one first locating feature.

6. The system of claim 1, wherein the at least one communications module comprises a sensor processor configured and arranged to receive the data from the sensors and a wireless communications unit configured and arranged to wirelessly transmit the sensor information to the external device.

7. The system of claim 1, wherein the plurality of sensors comprises the first accelerometer and at least one of c) a second accelerometer, a gyroscope, or a magnetometer.

8. The system of claim 1, wherein the plurality of sensors comprises at least one pulse sensor.

9. The system of claim 1, further comprising a patient device configured and arranged to receive the sensor information from the at least one communications module and to process the sensor information and display the processed sensor information for viewing by the patient.

10. The system of claim 1, further comprising a clinician device configured and arranged to receive the sensor information from the at least one communications module or from a patient device and to process the sensor information and display the processed sensor information for viewing by a clinician.

11. The system of claim 1, wherein a portion of at least one of the sensors extends through the single housing to provide access to the patient without an intervening portion of the single housing.

12. The system of claim 1, wherein the plurality of sensors comprises the first accelerometer and a second accelerometer arranged in-line with each other within the single housing.

13. The system of claim 1, wherein the system comprises the adhesive pad and the adhesive pad extends around a circumference of the housing of the sensor module.

14. A sensor module, comprising:
a housing configured and arranged to be disposed near a joint of a patient and adjacent to skin of the patient, wherein the housing has a first end and a second end opposite the first end, wherein the second end is narrower than the first end indicating to the patient that the second end is to be positioned on the skin of the patient pointed toward the joint;
a plurality of sensors disposed within the housing, wherein the plurality of sensors comprises at least one sensor configured and arranged to provide sensor data that can be processed to determine a range of motion of the joint;
a sensor processor disposed within the housing and coupled to the plurality of sensors and configured and arranged to receive sensor data from the plurality of sensors;
a communications unit disposed within the housing and coupled to the sensor processor and configured and arranged to transmit sensor information, based on the sensor data, to an external device; and
an adhesive pad coupleable to the housing and configured and arranged to adhesively adhere the sensor module to the skin of the patient for at least one hour, wherein the adhesive pad comprises at least one first locating feature and the housing comprises at least one second locating feature having a shape complementary to a shape of the at least one first locating feature to facilitate alignment of the adhesive pad with the housing.

15. The sensor module of claim 14, wherein one of the at least one first locating feature or the at least one second locating feature comprises a magnet and another one of the at least one first locating feature or the at least one second locating feature comprises a second magnet or a magnetically attractive material to facilitate coupling of the adhesive pad to the housing.

16. The sensor module of claim 14, wherein the plurality of sensors comprises a first accelerometer in combination with at least one of a second accelerometer, a gyroscope, or a magnetometer.

17. The sensor module of claim 14, wherein the plurality of sensors comprises at least two proximity sensors configured and arranged to provide sensor data that can be processed to determine a number of repetitions of joint movement.

18. The sensor module of claim 14, wherein the plurality of sensors comprises at least one temperature sensor or pulse sensor.

19. A system, comprising:
the sensor module of claim 14; and,
a second sensor module that is mechanically independent from the sensor module, wherein the second sensor module comprises
a second housing; and
a plurality of second sensors disposed within the second housing, wherein the plurality of second sensors comprises at least one second sensor configured and arranged to provide sensor data that can be processed to determine a range of motion of the joint.

20. The sensor module of claim 14, wherein the adhesive pad extends around a circumference of the housing.

* * * * *